United States Patent [19]

Boettcher

[11] Patent Number: 4,479,527
[45] Date of Patent: Oct. 30, 1984

[54] METHOD FOR FACILITATING THE MANUFACTURE OF A BONDABLE METALLIC SURFACE

[75] Inventor: Ralph A. Boettcher, La Verne, Calif.
[73] Assignee: Unitek Corporation, Monrovia, Calif.
[21] Appl. No.: 438,558
[22] Filed: Nov. 2, 1982
[51] Int. Cl.³ .............................. B22C 9/04; B22C 7/02
[52] U.S. Cl. ........................................ 164/34; 164/35;
                                                164/45; 433/180; 433/183
[58] Field of Search .................. 164/34, 35, 45, 246,
                                    164/DIG. 4; 433/180, 181, 182, 183

[56] References Cited

U.S. PATENT DOCUMENTS

| | | | |
|---|---|---|---|
| 1,436,016 | 11/1922 | DeNise | 433/180 |
| 2,889,598 | 6/1959 | Lundquist et al. | 164/246 |
| 2,936,490 | 5/1960 | Mason | 433/180 X |
| 3,063,113 | 11/1962 | Operhall et al. | 164/45 |
| 3,375,582 | 4/1968 | Myerson | 164/34 X |
| 4,172,323 | 10/1979 | Orlowski | 433/180 |
| 4,310,312 | 1/1982 | Keller et al. | 433/180 X |
| 4,360,342 | 11/1982 | Salvo | 433/180 X |

Primary Examiner—Nicholas P. Godici
Assistant Examiner—J. Reed Batten, Jr.
Attorney, Agent, or Firm—Stuart E. Krieger; Richard H. Brink; Isaac Jarkovsky

[57] ABSTRACT

A pad eliminatable by heat prior to casting has a patterned surface and a non-porous backing. The pad is sized and shaped into at least part of the appliance and the patterned surface is conformed to the desired bonding surface contour. The patterned surface yields irregularities in the cast bonding surface which increases bondability.

7 Claims, 19 Drawing Figures

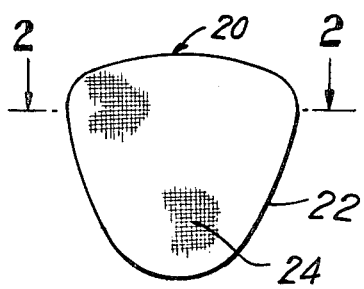
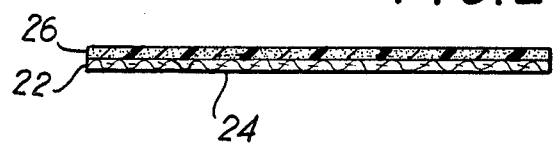
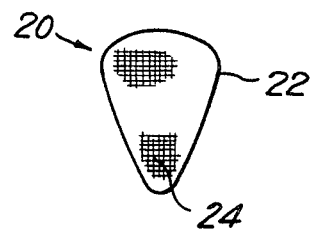
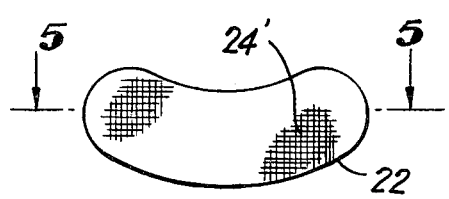
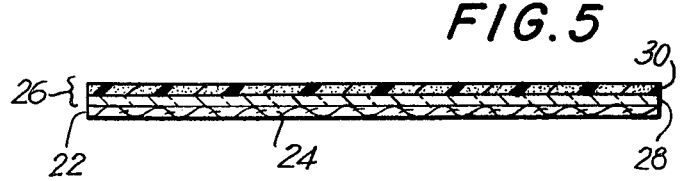
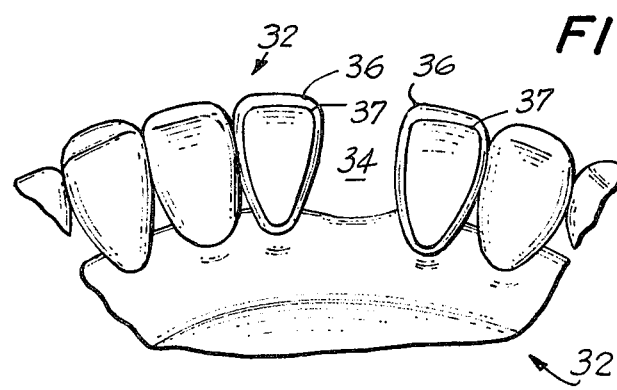

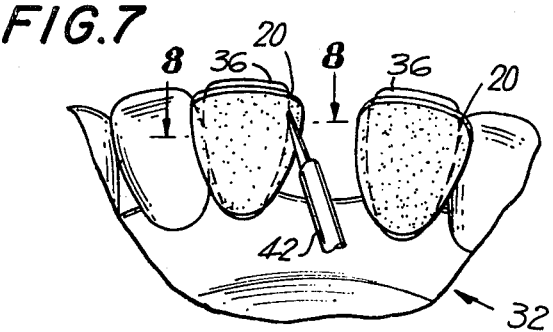
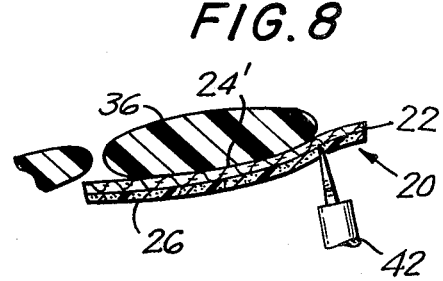
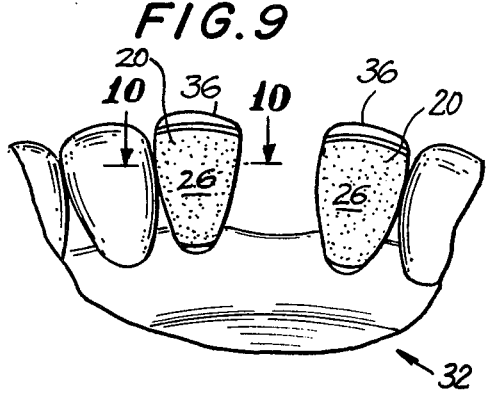
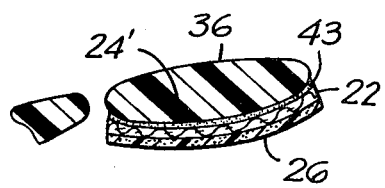
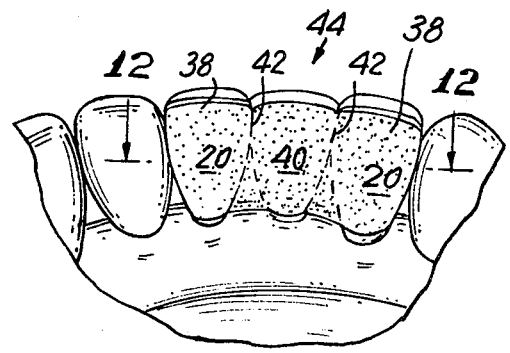

METHOD FOR FACILITATING THE MANUFACTURE OF A BONDABLE METALLIC SURFACE

BACKGROUND OF THE INVENTION

1. Field of the Invention

The present invention relates generally to casting and more particularly to an article having a pattern which is to be incorporated into the bonding surface of an appliance during its manufacture by investment casting and its method of incorporation.

2. Description of the Prior Art

The present invention is applicable to the casting of metallic appliances or devices requiring a surface which facilitates bonding by an adhesive, and is particularly suitable to the manufacture of dental appliances.

Bonding of intraoral dental appliances to the surfaces of teeth is frequently necessary during orthodontic treatment. Proper bonding with an adhesive necessitates the preparation of both the bonding surface of the appliance and the tooth surface. Conventionally, the tooth enamel is acid etched to enhance the bonding of the adhesive to the tooth. The bonding surface of an orthodontic appliance may be prepared by attaching a porous mesh bonding pad to the appliance by brazing, welding or sintering.

The surface of a cast dental appliance may be electrolytically etched. This approach is used in what has become known as the Maryland Bridge technique, popularized by Drs. Thompson and Livaditis at the University of Maryland. The Maryland Bridge typically consists of a central pontic with wing-like retainers at each end for attachment to abutment teeth. The bonding surface of the Maryland Bridge retainers are acid etched to create an irregular surface which increases its bondability to the surface of a tooth. In contrast with the earlier and traditional crown and bridge techniques the two abutment teeth, one on each of the opposite sides of the pontic, are not ground down, and the need for a partial denture is eliminated.

Disadvantages of the Maryland Bridge technique are that only the less corrosion resistant base metal alloys can be satisfactorily etched, and the etching process is itself difficult to control as the extent and evenness of the etch are dependent on the current, voltage, surface area and acid strength.

Problems that dental laboratories are faced with then practicing this technique involve the use of acids. Some dental laboratories are unaccustomed to using corrosive acids in their routine operation and such fluids may cause accidents. In addition, acid fumes require suitable exhaust ventilation, e.g. a chemical fume hood, which may be lacking in many smaller laboratories. A further drawback is that the equipment for etching is expensive, as it includes at a minimum an electroplating device with a stirrer and timer.

It is a primary object of the present invention to simplify the manufacture of an appliance having a bonding surface with irregularities, without using acid etching or the addition of a bonding pad to the cast article.

It is another object of the present invention to cast an appliance as a single element with a plurality of irregularities formed into the tooth abutting surface of the appliance.

It is also an object of the present invention to provide a preformed pad which is beneficially incorporated into a mold to form a patterned bonding surface.

It is a further object of the present invention to provide a device capable of producing a patterned bonding surface in corrosion resistant alloys, as well as etchable metallic alloys.

It is an additional object to provide a patterned bonding surface to an orthodontic appliance which achieves greater bonding strength with tooth enamel than devices presently available.

It is also an object of the present invention to simplify and reduce the time necessary for the fabrication of a dental bridge.

SUMMARY OF THE INVENTION

These and other objectives are accomplished by the present invention which includes a novel article structured for use in the lost wax investment casting process and the method of incorporating the article. The article is a pad which is eliminatable from the investment casting mold at temperatures typically employed during the lost wax process. These temperatures typically range from 1400°–2000° F. The pad includes a surface portion that is predeterminedly patterned so as to produce asperities in the casting surface derived from the patterned surface portion. The patterned surface portion has a backing portion affixed thereto which is non-porous.

The patterned surface portion is flexible so as to be conformable to a predetermined surface, but with sufficient rigidity to do so without creasing. When manufacturing dental appliances, the predetermined surface is typically taken off of a dental model and corresponds to the labial or lingual surface of the tooth to which the appliance is to be bonded. After conformation to the dental model, the patterned surface is fixed in shape so that upon removal from the predetermined surface, the patterned surface portion maintains the conformed surface contour. The fixation is provided at least in part by the non-porous backing portion. If desired, additional material, such as wax, may be added to the backing portion to provide additional rigidity, and/or the new material may be added for sculpturing to the shape of the dental appliance.

A method utilizing the above described pad for incorporation in the casting of an appliance so as to produce an irregular, asperity-ridden surface which facilitates adhesive bonding includes the following steps: sizing at least one pad so that the patterned surface portion approximates at least a portion of an appliance to be cast; attaching the patterned surface with suitable adhesive to a predetermined surface to be replicated; fixedly conforming the surface portion of the pad to said predetermined surface; investment casting said pad; and eliminating said pad from the casting mold with the heat employed during the lost wax investment process.

A particularly suitable use of the pad is in the fabrication of the wings of the Maryland Bridge.

BRIEF DESCRIPTION OF THE DRAWINGS

The foregoing and other objects, characteristics and advantages of the present invention will be more clearly understood from the following detailed description when read in conjunction with the accompanying drawings in which:

FIG. 1 is a front elevational view of a two-layered mesh pad in accordance with the present invention;

FIG. 2 is a cross-sectional view taken along line 2—2 of FIG. 1;

FIG. 3 is a front elevational view showing an alternative shape for a mesh pad, in accordance with the present invention;

FIG. 4 is a front elevational view showing a three-layered mesh pad with wider mesh openings than FIGS. 1-3 and an alternative shape;

FIG. 5 is a cross sectional view taken along line 5—5 of FIG. 4;

FIG. 6 is a perspective view from the lingual side of a portion of a dental model with the periphery of the abutment teeth on opposite sides of a missing tooth outlined on the model by a marker;

FIG. 7 is a perspective view from the lingual side showing the outlined shape of a tooth from a dental model being traced with a utensil on the pad backing;

FIG. 8 is a cross-sectional view taken along line 8—8 of FIG. 7;

FIG. 9 is a perspective view from the lingual side showing the abutment teeth with the pads properly sized and affixed;

FIG. 10 is a cross-sectional view taken along line 10—10 of FIG. 9;

FIG. 11 is a perspective view from the lingual side showing each of the two abutment teeth fitted with a pad and affixed to a wax pontic;

DESCRIPTION OF THE PREFERRED EMBODIMENTS

Figure 12:
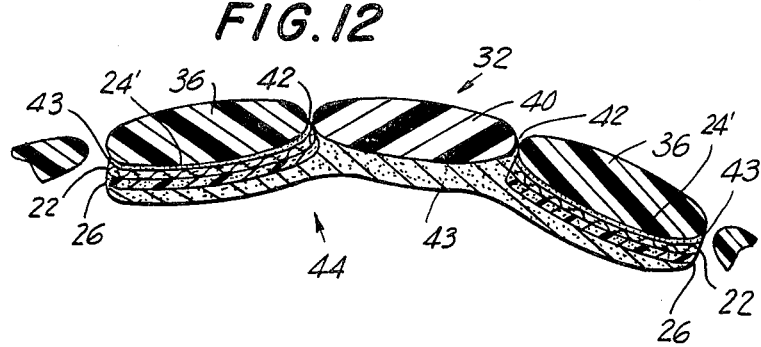
FIG. 12 is a cross-sectional view taken along line 12—12 of FIG. 11.

Referring now to the Figs. wherein a pad in accordance with the present invention is generally indicated by the numeral 20. The pad includes a surface portion 22 at least partly patterned 24 and a non-porous backing portion 26. The entire pad 20 is composed of material or materials which are eliminatable by the temperatures conventionally used in the lost wax technique of investment casting, typically in the range of 1400°–2000° F.

In FIGS. 1-4 the patterned surface portion 24 is a mesh or screen appropriate for the manufacture of a bonding surface for dental appliances. Preferably, the mesh is a Poly-Sieve woven polymer made of a polyethylene fiber. Other appropriate mesh materials are nylon and polyester. A wide range of mesh openings are suitable, including the range of 100 to 1,300 microns, and in fact mesh opening sizes of 202 microns and 432 microns produced a cast bonding surface having acceptable bond strengths. It has been found, however, that the 202 micron mesh size conforms more readily to the surface of a tooth model to be replicated by casting. For dental applications, the thickness of such preformed patterns typically range from 0.2 to 0.1 mm, with a preference at about 0.5 mm. The backing portion is preferably a non-porous pressure sensitive wax. A gauge of 26 has been found to be particularly suitable. The backing portion is affixed to the patterned surface portion 24 by an appropriate adhesive, e.g. 3M 4693 plastic adhesive.

Numerous pattern materials are appropriate for the surface portion 22. In fact, the predeterminedly patterned surface portion 24 need not contain openings. The pattern 24 must, however, contain an adequate number of indentations and/or protrusions to provide a roughened bonding surface in the cast article derived therefrom.

In addition, the pattern must be suitably flexible to conform to the shape of the surface requiring replication without creasing. The pads are preferably preformed into shapes suitable for dental applications. An alternative shape for a preformed pad is shown in FIG. 3.

FIGS. 4 and 5 show a pad 20 having a surface portion 22 with a predetermined surface pattern 24' having wider mesh openings than the pad of FIGS. 1-3. The backing portion 26 affixed thereto is provided with a barrier layer 28 composed of a material which prevents the pressure sensitive wax portion 30 from penetrating the mesh, and otherwise diminishing the bonding strength of the cast bonding surface. Cellophane and polypropylene are very effective materials for the barrier layer 28. Pressure is applied to the wax portion 30 when the pad patterned surface portion 24 is conformed or shaped to the surface requiring replication.

A particularly preferred embodiment of this three type layer of pad includes a 202 micron woven Poly-Sieve screen as the surface patterned portion 24, and a barrier layer 28 of a clear polypropylene plastic sheet 0.0022 mm thick attached to the screen by an adhesive, and a non-porous 26 gauge pressure sensitive wax affixed to the barrier layer 28, also with an adhesive. An appropriate adhesive for both interfaces is 3M plastic adhesive 4693.

A preferred use of the pads involves the fabrication of a bridge. FIG. 6 is a schematic partial view of a stone dental model, generally indicated by the numeral 32, of a patient's mouth, as seen from the lingual side. A space 34 exists where a tooth is missing. The periphery of the two abutment teeth 36 are outlined 37 on the dental model 32 and a preformed pad 20, in this case the two-layered embodiment depicted in FIG. 3, is selected from an assortment of pads for each of the abutment teeth 36. The pads 20 should approximate, but yet be larger than, the shape of the desired retainers or wings 38, one of which will be positioned on each side of a fabricated pontic 40 (FIG. 11). The patterned surface portion or mesh 24' will correspond to the bonding surface of each retainer 38. As shown here, the bonding surface of each retainer wing 38 will correspond in surface area and shape of the lingual side of each abutment tooth 36.

As shown in FIGS. 7 and 8, the pads 20 are placed against the abutment teeth 36 of the model 32 with the patterned mesh portion 24' against the lingual surface. The outline 37 of the periphery marked on the dental model 32 is traced by an appropriate tool 42 onto the non-porous backing portion or wax side 26 of the pad 20. The pads 20 are removed and cut along the traced line with an appropriately curved scissor, such as the Unitek Curved Scissor Model 801002, so as to yield a pad corresponding to the exact size of the lingual side of each of the abutment teeth 36.

An appropriate temporary adhesive 43 is applied to each of the abutment teeth 36 so as to cover the entire lingual side. Each of the pads 20 are then properly positioned on the abutment tooth 36 with the patterned mesh surface portion 24' against the adhesive 43, as shown in FIGS. 9 and 10. Thus, the mesh or patterned surface portion 24 of each pad 20 will contact the adhesive 43 and the backing portion 26 will extend toward the inner portion of the dental model 32.

The pads 20 are conformed to the predetermined lingual surface by applying pressure to the backing portion 26 of the pads 20 with an appropriate utensil.

Referring now to FIGS. 11-16, a preformed wax pontic 40, built in a manner well-known in the art, is positioned in the space 34. An appropriate non-porous wax, which may be the same wax as used in the backing portion 26, is then applied at 42 to attach the pontic 40 to the backing portion 26 of the pads 20 affixed to each of the model abutment teeth 36. More non-porous wax may be added to the backing portion 26 of the pads 20 and pontic 40 to provide additional rigidity and/or to be sculptured into the desired shape of the retainers 38. At this point, the three part bridge, composed of two wings or retainers 38 sandwiching a pontic 40 and generally designated by the numeral 44, appears as shown in FIGS. 11 and 12, and is referred to as a wax-up.

The stone dental model 32 is soaked in water and the three part wax-up 44 of the bridge is released. The temporary adhesive 43 is removed from the patterned surface portion or mesh 24 by brushing the mesh 24' under cold running water. The wax-up 44 is then prepared for investment casting using the lost wax process which is well-known in the art. However, prior to complete investment, the investment material, e.g. Vestra ™, is gently worked into the mesh openings of the patterned surface portion 24' so as to insure duplication of the mesh pattern in the cast bonding surface on the bonding surface of the retainers 38.

Figure 13:
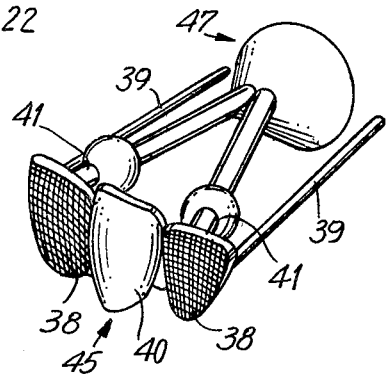
FIG. 13 is a perspective view of a disposable bridge casting support sprue with the pontic and retainer wings attached thereto.

FIG. 13 shows an investment casting 45 of the wax-up 44 mounted on a disposable bridge casting support 47 of a type known in the art, with the appropriate sprues 39 and vents 41 still attached.

Figure 14:
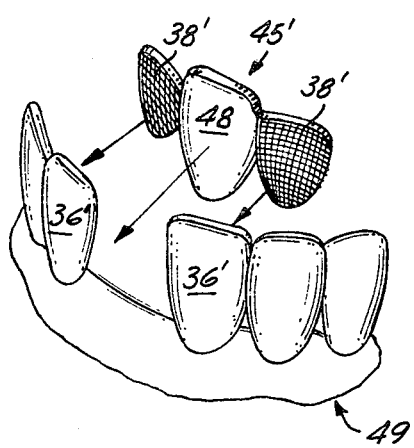
FIG. 14 is a perspective view from the labial side showing the cast pontic and retainer wings positioned for insertion according to the arrows.

The wax up of the investment casting 45 is removed preferably with heat. This is typically done at the aforementioned temperatures of 1400°-2000° F., appropriate to the lost wax process. A solid metal casting 45' (FIG. 14) of the dental bridge is then prepared from the investment casting which is composed of the pontic 40', and metal retainer wings 38'. The pontic portion 40' is coated with porcelain 48 by known methods so that the bridge appears as shown in FIG. 14. The finished bridge is positioned for insertion in the patient's jaw 49 between the patient's abutment teeth 36'.

Figure 15:
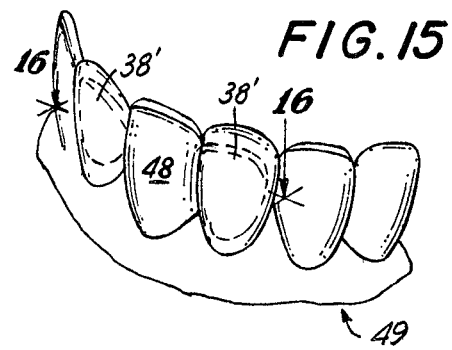
FIG. 15 is a perspective view from the labial side of the pontic and retainer wings in place, as indicated by the phantom lines.
Figure 16:
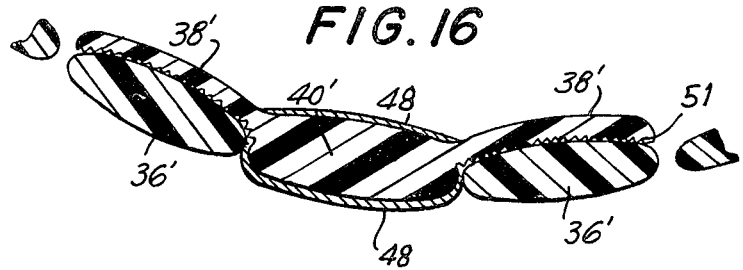
FIG. 16 is a cross-sectional view taken along line 16—16 of FIG. 15.

As shown in FIGS. 15 and 16, the bridge is not visible from the labial side as the metallic mesh patterned bonding surface of each metal retainer 38', derived from the patterned surface portion 24 of the pad 20, abuts the lingual surface of an abutment tooth 36'.

A permanent adhesive 51 is placed on the lingual side of the abutment teeth, and the wings 38' are affixed thereto.

Figure 17:
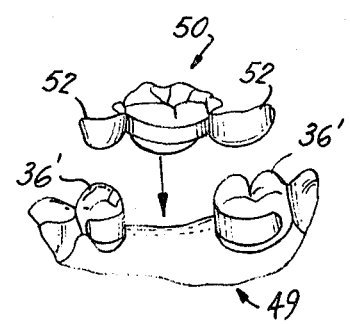
FIG. 17 is a perspective view from the lingual side showing the prior art Maryland Bridge.

FIG. 17 shows the prior art Maryland Bridge 50 with acid etched retainer wings 52 as seen from the lingual side positioned for insertion into the patient's jaw 49.

Figure 18:
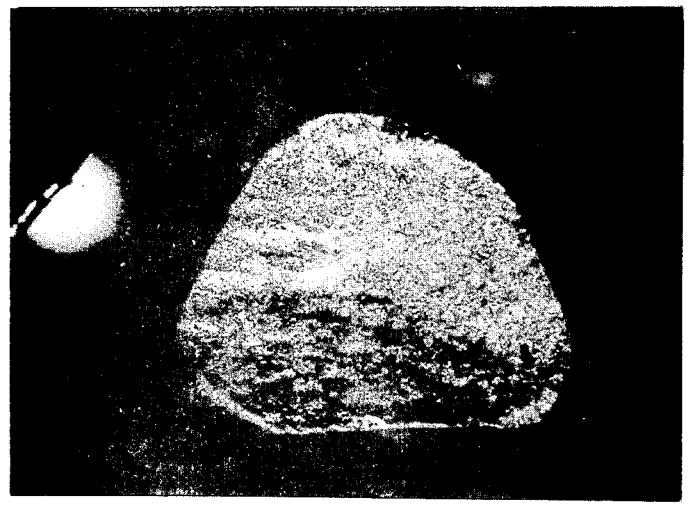
FIG. 18 is a photomicrograph showing the tooth abutting surface of the etched wing of a Maryland Bridge at 9× magnification.
Figure 19:
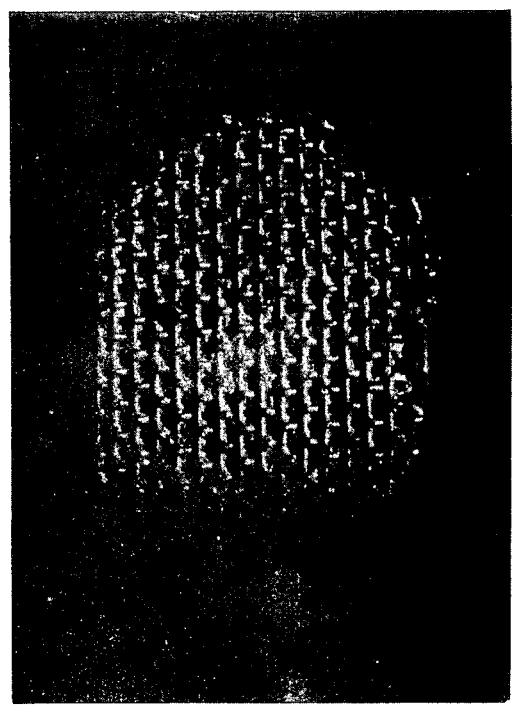
FIG. 19 is a photomicrograph showing the bonding surface of an article manufactured with a pad in accordance with the present invention at 9× magnification.

FIGS. 18 and 19 show the contrast between an etched wing 52 (FIG. 11) of the prior art Maryland Bridge, and the cast mesh patterned bonding surface of the wing 38' produced with a pad 20 of the present invention. Each is shown at a 9× magnification. Clearly, the surface irregularities of the cast mesh pattern retainer wings 38', achieved with the aid of the pads 20 of the present invention, are of greater depth and frequency than those of the etched wings 52'. Test results indicate that superior bonding is achieved with the pad of the present invention.

A peel/shear bond strength test was used to determine the bond strength of dental appliances prepared using the present invention and method as compared to the bonding techniques presently available. According to the testing procedure, bovine teeth are mounted in acrylic so as to expose the labial surface on which test samples are bonded, using etching and bonding techniques. A no-mix adhesive known as Unite, a trademark of Unitek Corp., and a conventional adhesives known as Concise, a trademark of 3M Company, were used. The acrylic mounts are placed vertically in an Instron Universal Testing Machine. The test samples were peeled/sheared off the bovine tooth through a wire looped around the "bracket" side of the appliance. The following three types of orthodontic brackets were tested: (1) an acid etched base; (2) cast mesh base; and (3) sintered wire base. In addition, etched and cast mesh wing portions of a bridge customized to bovine teeth were evaluated. As shown in Table I below, the predeterminedly patterned or cast mesh porous surface produced in accordance with the present invention exhibited the highest bond strength in both types of test samples, and tooth fracture was often encountered.

TABLE I

| Type of Bonding | Average Bond Strength (lbs.) |
| --- | --- |
| Acid etched bracket base | 26 |
| Cast mesh bracket base | 62 |
| Sintered wire mesh base | 41 |
| Acid etched wings | 84 |
| Cast mesh wings | exceeds 143 or fracture strength of the tooth |

It should be noted that the cast mesh retainers of wings are larger in contact area than the rest of the bonding bases. Generally, twelve tests were conducted on each type for averaging. In the twelve tests conducted on the cast mesh retainers, test fixture wire failure, tooth failure and tooth holder failure occurred repeatedly and, consequently, only a lower limit for the bond strength can be established.

While the invention has been described above with respect to specific embodiments, it should be clear that these embodiments are given by way of example and shall not be deemed as limiting the scope of the invention, except in accordance with the claims hereof.

The invention claimed is:

1. A method for casting an appliance having a bonding surface which facilitates adhesive bonding thereof, comprising the steps of:

sizing at least one pad to approximate at least a portion of an appliance to be cast, said pad having a surface portion at least partly predeterminedly patterned for producing asperities in a casting surface derived therefrom, and a non-porous backing, said pad being eliminatable at temperatures, employed during lost wax investment casting;

attaching said patterned surface portion with a suitable adhesive to a predetermined surface to be replicated;

fixedly conforming said surface portion to said predetermined surface;

removing said pad from said predetermined surface;

investment casting said pad to form a mold; and eliminating said pad from the investment casting mold.

2. The method of claim 1 further comprising the step of preparing a metal casting from said investment casting mold.

3. The method of claim 1 wherein the steps of sizing include:

applying an oversized pad to the predetermined surface;

outlining said predetermined surface periphery on said pad;

removing said pad from the predetermined surface; and cutting said pad along said outline.

4. The method of claim 1 wherein said predetermined surface is on a dental model.

5. The method of claim 1 wherein said predetermined surface is on the lingual side of the dental model.

6. The method of claim 1 wherein the step of fixedly conforming said surface portion to said predetermined surface includes adding additional material to said backing portion.

7. A method for casting a dental bridge having a bonding surface which facilitates adhesive bonding thereof, comprising the steps of:

sizing two pads to approximate retainer wings of a bridge to be cast, said pads each having a surface portion at least partly predeterminedly patterned for producing asperities in a casting surface derived therefrom, and a non-porous backing, each of said pads being eliminatable by heat employed during lost wax investment casting;

attachng said patterned surface portion of each pad with a suitable adhesive to an abutment tooth surface;

fixedly conforming each surface portion to the respective tooth surface;

attaching each of said pads to a wax pontic positioned therebetween, to form a wax-up of a bridge;

removing said wax-up from the tooth surfaces;

investment casting said wax-up to form a model;

eliminating said pads from investment casting model; and preparing a metal casting from the investment casting model.

* * * * *